(12) United States Patent
Kesten et al.

(10) Patent No.: US 6,251,104 B1
(45) Date of Patent: *Jun. 26, 2001

(54) GUIDING CATHETER SYSTEM FOR ABLATING HEART TISSUE

(75) Inventors: Randy J. Kesten, Mountain View; Manuel A. Javier, Jr., Santa Clara, both of CA (US)

(73) Assignee: Eclipse Surgical Technologies, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,530

(22) Filed: Oct. 31, 1997

Related U.S. Application Data

(63) Continuation-in-part of application No. 08/646,856, filed on May 8, 1996, which is a continuation-in-part of application No. 08/438,743, filed on May 10, 1995, now abandoned.

(51) Int. Cl.[7] ..................................................... A61N 5/06
(52) U.S. Cl. .................................. 606/15; 606/7; 606/46; 606/170; 604/22; 604/158; 604/264
(58) Field of Search ..................................... 604/289, 158, 604/264, 22; 606/7, 10–17, 167, 169, 170, 45, 46

(56) References Cited

U.S. PATENT DOCUMENTS

| | | |
|---|---|---|
| 4,581,017 | 4/1986 | Sahota . |
| 4,658,817 | 4/1987 | Hardy . |

(List continued on next page.)

FOREIGN PATENT DOCUMENTS

| | | | |
|---|---|---|---|
| 9215779 | 2/1993 | (DE) | ............................. A61M/25/00 |
| 295 01 973 U | 4/1995 | (DE) . | |

(List continued on next page.)

OTHER PUBLICATIONS

International Searching Authority communication, "International Search Report", dated Feb. 16, 1999.

Mirhoseini "Laser Applications in Thoracic and Cardiovascular Surgery" *Medical Instrumentation*, 17(6):401–403 (Nov.–Dec. 1982).

(List continued on next page.)

*Primary Examiner*—David M. Shay
(74) *Attorney, Agent, or Firm*—Heller Ehrman White & McAuliffe LLP

(57) ABSTRACT

A guiding catheter system for delivering an elongated therapeutic or diagnostic device into a patient's left ventricle which includes a first guiding catheter with a shaped distal extremity configured to be aligned with or parallel to a longitudinal axis or long dimension of the patient's left ventricle and a second guiding catheter slidably and rotatably disposed within an inner lumen of the first guiding catheter which has a shaped distal shaft section and an inner lumen configured to slidably receive an elongated therapeutic or diagnostic device such as a tissue ablation device, e.g. an optical fiber connected to a laser source, an ultrasonic energy emitting device or a radio frequency energy emitting device. The shaped distal section of the first guiding catheter is shaped or is shapable within the patient's heart chamber. The second guiding catheter is advanced out of the inner lumen of the first guiding catheter until the distal end extends out of the port in the distal end of the first guiding catheter and provides a passageway for the therapeutic or diagnostic device to engage the endocardium surface at a perpendicular or near perpendicular orientation.

54 Claims, 6 Drawing Sheets

U.S. PATENT DOCUMENTS

| | | |
|---|---|---|
| 4,773,413 | 9/1988 | Hussein et al. . |
| 4,860,743 | 8/1989 | Abela . |
| 4,890,898 | 1/1990 | Bentley et al. . |
| 4,917,084 | 4/1990 | Sinofsky . |
| 4,967,745 | 11/1990 | Hayes et al. . |
| 4,985,028 | 1/1991 | Isner et al. . |
| 4,985,029 | 1/1991 | Hoshino . |
| 4,997,431 | 3/1991 | Isner et al. . |
| 5,093,877 | 3/1992 | Aita et al. . |
| 5,104,393 | 4/1992 | Isner et al. . |
| 5,106,386 | 4/1992 | Isner et al. . |
| 5,125,926 | 6/1992 | Rudko et al. . |
| 5,183,470 | 2/1993 | Wettermann . |
| 5,267,982 | 12/1993 | Sylvanowicz . |
| 5,380,316 | 1/1995 | Aita et al. . |
| 5,389,096 | 2/1995 | Aita et al. . |
| 5,427,119 | 6/1995 | Swartz et al. . |
| 5,497,774 | 3/1996 | Swartz et al. . |
| 5,575,766 | 11/1996 | Swartz et al. . |
| 5,628,316 | 5/1997 | Swartz et al. . |
| 5,632,734 | 5/1997 | Galel et al. . |
| 5,690,611 | 11/1997 | Swartz et al. . |

FOREIGN PATENT DOCUMENTS

| | | | |
|---|---|---|---|
| 0 277 366 | 8/1988 | (EP) . | |
| 277366 | * 8/1988 | (EP) | ................................. 604/289 |
| 0 416 793 | 3/1991 | (EP) . | |
| 0 448 859 | 10/1991 | (EP) . | |
| 0 515 867 | 12/1992 | (EP) . | |
| 0 670 168 | 9/1995 | (EP) . | |
| 0 727 236 | 8/1996 | (EP) . | |
| 0 727 239 | 8/1996 | (EP) . | |
| 0728494 | 8/1996 | (EP) | ............................ A61M/25/00 |
| WO 92/12754 | 8/1992 | (WO) . | |
| WO 94/02077 | 2/1994 | (WO) . | |
| WO 95/08364 | 3/1995 | (WO) . | |
| WO 96/30072 | 10/1996 | (WO) | ........................... A61M/29/00 |
| WO 96/35469 | 11/1996 | (WO) . | |

OTHER PUBLICATIONS

Mirhoseini "Laser Revascularization of the Heart" *New Frontiers in Laser Medicine and Surgery* 296–303 (1982).

Mirhoseini et al. "Lasers in Cardiothoracic Surgery" *Lasers in General Surgery* 216–232 (1989).

Mirhoseini et al. "Myocardial Revascularization by Laser: A Clinical Report" *Lasers in Surgery and Medicine* 3:241–245 (1983).

Mirhoseini et al. "New Concepts in Revascularization of the Myocardium" *A Torac. Surg.* 45:415–420 (Apr. 1988).

Mirhoseini et al. "Revascularization of the Heart by Laser" *Journal of Microsurgery* 253–260 (Jun. 1981).

Mirhoseini et al. "Transvenicular Revascularization by Laser" *Lasers in Surgery and Medicine* 2:187–198 (1982).

Mirhoseini et al. "Clinical Report: Laser Myocardial Revascularization" *Lasers in Surgery and Medicine* 6:459–461 (1986).

Walter et al. "Treatment of Acute Myocardial Infarction by Transmural Blood Supply from the Ventricular Cavity" *Europ. Surg. Res.* 3:130–138 (1971).

* cited by examiner

GUIDING CATHETER SYSTEM FOR ABLATING HEART TISSUE

RELATED APPLICATIONS

This application is a continuation-in-part of application Ser. No. 08/646,856, filed on May 8, 1996, entitled SYSTEM AND METHOD FOR TREATING OR DIAGNOSING HEART TISSUE, which is a continuation-in-part of copending application Ser. No. 08/438,743, filed on May 10, 1995 now abandoned, entitled DELIVERY SYSTEM AND METHOD FOR MYOCARDIAL REVASCULARIZATION, both of which are incorporated herein in their entirety by reference.

BACKGROUND OF THE INVENTION

This invention relates to elongated devices for therapeutic or diagnostic procedures in a wall of a patient's heart, particularly to the treatment of myocardial tissue experiencing ischemic conditions, by revascularization of such myocardial tissue.

Myocardial revascularization typically involves formation of one or more channels in a patient's heart wall which defines the heart chamber, particularly the left ventricle. The first trials of the revascularization process were apparently made by Mirhoseini et al. See for example the discussions in Lasers in General Surgery (Williams & Wilkins; 1989), pp 216–223. Other early disclosures of this procedure are found in an article by Okada et al. in Kobe J. Med. Sci 32, 151–161, October 1986 and in U.S. Pat. No. 4,658,817 (Hardy). Both of these references describe intraoperative revascularization procedures which require the chest wall to be opened and which include formation of the revascularization channels completely through the heart wall, i.e. the epicardium, the myocardium and the endocardium.

Copending application Ser. No. 08/078,443, filed on Jun. 15, 1993 (Aita et al.), which is incorporated herein in its entirety, describes an intravascular system for myocardial revascularization which is introduced percutaneously into a peripheral artery and advanced through the patient's arterial system into the left ventricle of the patient's heart. The revascularization channels are not usually formed through the entire heart wall but only the endocardium and into the myocardium from within the left ventricle. This procedure eliminates the need of the prior intraoperative procedures to open the chest cavity and to penetrate through the entire heart wall in order to form the channel through the endocardium into the myocardium. While the percutaneous method and system for introducing the revascularization device developed by Aita et al. represents a substantial advance, one of the difficulties in forming revascularization channels from within a patient's left ventricle by means of a percutaneously introduced revascularization system has been accurately directing the distal tip of the channel forming device to a desired region of the patient's endocardium and maintaining the placement of the distal end of the channel forming device against a desired region of the ventricular wall at a proper angle, i.e. perpendicular or near perpendicular to the endocardium, while the heart is beating. Maintaining placement of the operative distal tip of the device is important because lateral displacement can affect the channel formation within the heart wall. The anatomy of human hearts and particularly the relationship of the ascending aorta and the left ventricle can vary considerably from patient to patient. The entry angle from the ascending aorta through the aortic valve into the left ventricle of a human heart does not facilitate the easy access to the free wall of the patient's heart which in substantial part defines the left ventricle. Direct entry from the ascending aorta through the aortic valve usually leads into the cordae tendonae of the mitril valve and to the posterior sulcus adjacent to the inferolateral papillary muscle to which the cordae are attached. As a result, the distal extremity of a guiding catheter advanced into the left ventricle through the aortic valve from the ascending aorta can inadvertently become entrapped or entangled with the cordae tendonae or be positioned in the posterior sulcus adjacent to the base of the inferolateral papillary muscle.

What has been needed is an improved delivery system and method for delivering a channel forming or other ablation device within the patient's heart chamber, particularly via percutaneous introduction into the patient's vasculature, which provides for an easy and accurate placement of the device against a desired region of the endocardium at the desired orientation and the maintenance of the position of the device within the patient's heart chamber while tissue is being ablated and the heart is beating. The present invention satisfies these and other needs.

SUMMARY OF THE INVENTION

The present invention is directed to a system for delivering an elongated therapeutic or diagnostic device into the interior of a patient's heart chamber that provides access to a wide region of the patient's endocardium defining at least in part the heart chamber. Additionally, the system disclosed accurately places and effectively holds the operative distal end of the device at a desired location within the patient's heart chamber. One embodiment of the present invention may be used to form a channel into the wall defining the heart chamber or to perform other treatments or diagnosis. The system also allows the position of the operative distal end of the device to be readily changed to facilitate performing therapeutic or diagnostic procedures at a plurality of locations within the heart chamber at a desired perpendicular or near perpendicular orientation with respect to the patient's endocardium.

The guiding catheter system of the invention generally includes a first guiding or delivery catheter which has a relatively straight main shaft section and a shaped distal shaft section having a discharge axis selected so that is generally aligned with or parallel to the longitudinal axis of the patient's left ventricle, and a second guiding or delivery catheter slidably and rotatably disposed within an inner lumen of the first guiding catheter and provided with a shaped distal section configured to have a discharge axis which is normal or near normal to the patient's endocardial layer which defines in part the left ventricle.

In accordance with the present invention the first guiding catheter has proximal and distal ends, a port in the distal end and an inner lumen extending within the catheter to the port in the distal end. The first guiding catheter has a relatively straight main. shaft section and a preshaped distal section configured to point in a direction so that the discharge axis of this catheter is aligned with or parallel or near parallel to the longitudinal axis of the left ventricle. For many applications the first guiding catheter is about 90 to about 130 cm, preferably about 100 to about 120 cm in length.

In one presently preferred embodiment of the invention, the first guiding catheter has a main shaft section and a shaped distal section with a proximal and distal angled segments which provide a discharge axis approximating the longitudinal axis or long dimension of the heart chamber.

In this embodiment the first segment of the distal shaft section is at an angle of about 95° to about 160°, preferably about 100° to about 140° with respect to a proximally adjacent second segment of the distal shaft section and the proximally adjacent second segment is at an angle of about 95° to about 160°, preferably about 100° to about 135° with respect to either the proximally adjacent main shaft section or a third segment of the distal shaft section proximally adjacent to the second segment. If there is a third segment of the distal section, it is at an angle of about 110° to about 170°, preferably about 120° to about 150° with respect to proximally adjacent main shaft section. The first and second segments should each be about 0.5 to about 5, preferably about 0.5 to about 4 cm in length, with the total length of the shaped distal section with two segments being about 2 to about 6 cm. If the distal section has a third segment, it should have a length of about 1 to about 5 cm, preferably about 2 to about 4 cm. The length of the shaped distal section with three segments should be about 3 to about 8 cm, preferably about 4 to about 7 cm.

In another presently preferred embodiment, the shaped distal section of the first guiding catheter has a single angled segment which provides a discharge axis approximating the longitudinal axis or long dimension of the heart chamber. In this embodiment the single angled segment of the distal shaft section has a length of about 2 to about 8 cm, preferably about 4 to about 6 cm and is at an angle of about 95° to about 160°, preferably about 100° to about 140° with respect to a proximally adjacent portion of the main shaft section.

The second guiding catheter of the invention is longer than the first guiding catheter, and is slidably and preferably rotatably disposed within inner lumen of the first guiding catheter. The second guiding catheter likewise has proximal and distal ends, a port in the distal end and an inner lumen extending within the second guiding catheter to the port in the distal end. The second guiding catheter has a relatively straight main shaft section and a distal section which is at an angle of about 80° to about 140°, preferably about 90° to about 120° with respect to the main shaft section thereof. The second guiding catheter should be at least 10 cm longer, preferably about 15 to about 50 cm longer, than the first guiding catheter and is about 100 to about 150 cm, preferably about 110 to about 140 cm in length. The shaped distal section of the second guiding catheter should have a radius of curvature of about 2 to 30 mm, preferably about 4 to about 20 mm between the main shaft section and the exit or discharge axis through the port in the distal end of the shaped distal section. The length of the shaped distal section is about 0.5 to about 4 cm, preferably about 1 to about 3 cm.

The angles of the various segments of the distal section of the first catheter and the angle of the second guiding catheter facilitate directing the operative distal end of an elongated therapeutic or diagnostic device which is slidably disposed within the inner lumen of the second guiding catheter toward the region of the endocardium where the procedure is to be performed at an orientation that is preferably perpendicular or near perpendicular with the endocardial surface of the patient's heart wall.

A presently preferred elongated therapeutic or diagnostic device is a system for ablating tissue within the wall of the patient's heart, particularly for the revascularization of an ischemic region thereof. The ablation system is adapted to emit ablation energy from its distal end which may be based on laser, radio frequency, ultrasonic or other high energy emissions. The ablation system is slidably disposed within the inner lumen of the second guiding catheter and is long enough so that the distal operative end extends out the port in the distal end of the second guiding catheter and contacts the endocardium and proximal end which extends out the proximal end of the second guiding catheter and can be operatively connected to a source of ablation energy such as laser, RF, ultrasound and the like. Preferably, the distal extremity of the ablation system which extends out the distal end of the guide catheter has sufficient rigidity to be self-supporting within the environment of the heart chamber.

In a presently preferred embodiment of practicing the method of the invention, the first guiding catheter of the delivery system is introduced into a peripheral artery, such as the femoral artery, and advanced through the patient's arterial system until the distal end of the first catheter is disposed within the patient's left ventricle. The position of the first guiding catheter is adjusted by the physician under fluoroscopic observation or other techniques until the distal tip is oriented generally along or parallel to the longitudinal axis of the left ventricle. The second guiding catheter is advanced through the previously introduced first guiding catheter which has a distal end appropriately positioned within the left ventricle. The second guiding catheter is rotatably and slidably disposed within the inner lumen of the first delivery catheter to facilitate the desired placement and orientation of the shaped distal section of the second guiding catheter within the left ventricle normal to the endocardium. In this manner the elongated therapeutic or diagnostic device slidably disposed within the inner lumen of the second guiding catheter is properly oriented with respect to the endocardial surface of the heart chamber in order to effectively couple emitted ablation energy to the tissue of the heart wall. Additionally, such perpendicularity helps to maintain the position of the distal end of the device, particularly a channel forming device, against the heart wall during multiple heart cycles. Without such perpendicular orientation, the operative tip of the therapeutic or diagnostic device tends to move laterally while the heart is beating resulting in mislocation of the channel, or ablated tissue or medical procedure.

The longitudinal and rotational movements of the first and second guiding catheters, particularly when the distal extremity of both are shaped, provide access to a wide region of the patient's endocardial surface and allow for the accurate placement of the operative end of the therapeutic or diagnostic device within the patient's left ventricle in a number of positions. The location of the distal end of the therapeutic or diagnostic device within the heart chamber, and particularly with respect to the endocardial surface, can be detected fluoroscopically by providing a radiopaque marker on the distal extremities of the ablation device and each of the guiding catheters. The use of dye injections through a port in the distal end of first and/or the second guiding catheter may be employed to further facilitate the location of the distal end of these catheters. Other means such as a variety of proximity detectors may be employed to detect contact between the distal end of the therapeutic or diagnostic device or the delivery catheters and the endocardium.

The distal sections of the first and second delivery catheters are preferably preformed into a desired shape so that they will provide a desired orientation for the delivery system when they extend into the patient's heart chamber. However, the catheters may alternatively be provided with control lines or other suitable means (e.g. a shape memory or a superelastic or pseudoelastic NiTi element) to deflect or otherwise shape the distal sections of the catheters once the distal extremity of the delivery system extends into the heart chamber.

With the system of the invention, essentially the entire semi-conical inner surface of the free wall defining part the patient's heart chamber and the intraventricular septum are accessible at a desired normal or near normal orientation by rotating one or both of the guiding catheters.

The first and second guiding catheters are preferably relatively stiff catheters so that the position of the therapeutic or diagnostic device disposed within the inner lumen of the second guiding catheter and extending out the port in the distal end thereof will be maintained during the procedure even though the heart is beating and blood is flowing within the chamber. A supporting sheath may be disposed within the inner lumen of the second guiding catheter which is extended to the surface of the heart wall, to further support the therapeutic or diagnostic device if the ablation device is insufficiently self supporting.

The anatomy of the left ventricle can vary considerably from patient to patient as to dimensions and shape. As a result, in some instances the ablation device may not be able to be directed to the entire region to be treated, particularly in the apex region of the heart chamber where the shape of the second guiding catheter may not be suitable to maintain a perpendicular orientation. In this case, the shape of the distal section of the second guiding catheter can be adjusted to another, more suitable angle to ensure a normal orientation between the operative distal end of the ablation device and the endocardial surface by pulling the second guiding catheter back into the inner lumen of the first guiding catheter a short distance so that part of the shaped distal section is pulled back into the inner lumen of the first guiding catheter. This changes the angle of the particular distal segment with respect to an adjacent segment or an adjacent portion of the main shaft section. Thus, normal or near normal orientation can be maintained in these difficult to reach regions.

While the present invention is described in terms of guiding catheters having permanently shaped distal sections, those skilled in the art will recognize that the distal section which can be deformed or shaped once positioned within the patient's heart chamber by means such as control wires or strands or by controlling the temperature of a shape memory element within the distal section, in order to facilitate directing the distal portion of the channel forming device or other type of ablation device, toward the region of the endocardium where the procedure is to be performed. A variety of other means may be employed to provide shape to the distal extremities of the guiding catheters.

In one presently preferred embodiment, the ablation or channel forming device is an elongated optical fiber system slidably disposed within the inner lumen of the second guiding catheter. The orientation of the distal extremity of the optical fiber system, controlled by the exit or discharge axis of the distal section of the second guiding catheter, is directed to the area of the endocardium to be ablated or into which a channel is to be formed, is perpendicular or nearly perpendicular to the endocardial surface of the patient's heart wall. The optical fiber system is preferably a laser based optical fiber system for forming channels within the wall of the patient's heart. The distal extremity of the optical fiber system which extends out the distal end of the second guiding catheter is sufficiently stiff to be self-supporting, i.e. it does not sag significantly when unsupported, and can be pressed against the endocardial or myocardial surface with sufficient pressure while forming the channel or performing ablation or other procedure without collapsing. Generally, the distal section of the optical fiber is considered as being "self supporting" if a force of at least 4 grams, preferably at least 8 grams, is required to deflect the free end of a cantilevered specimen 0.5 inch (12.7 mm) in length (span length) of the optical fiber a distance of one millimeter.

In a presently preferred embodiment of practicing one aspect of the invention, the system is introduced into a peripheral artery, such as the femoral or brachial artery, and advanced through the patient's arterial system until the shaped distal portion of the first guiding catheter is disposed within the patient's left ventricle. The second guiding catheter may be advanced through and out the port in the distal end of the first guiding catheter where it is oriented toward the heart wall. The perpendicular or near perpendicular orientation of the distal extremity of the elongated optical fiber system with respect to the endocardial surface of the heart chamber is required in order to effectively couple the ablation energy emitted from the distal end of the optical fiber system to the tissue. Additionally, such perpendicularity helps to maintain the position of the distal end of the optical fiber system against the tissue to be ablated or removed to form the channel. If not pressed against the endocardial tissue in a relatively normal orientation, the operative distal tip tends to move laterally while the heart is beating resulting in mislocation of the channel, or ablation of tissue outside the desired region. As used herein the terms "normal" and "perpendicular" shall include variations of up to 30° from a normal or perpendicular orientation.

The longitudinal and rotational movements of the guiding catheters provide access to a wide region of the patient's endocardial surface from within the heart chamber and allows for the accurate placement of the operative distal end of the ablation device within the patient's left ventricle in a number of positions. With the system of the invention, essentially the entire inner surface of the wall defining the patient's heart chamber is accessible to deliver an elongated ablation device to the desired location with the desired orientation while the heart is beating.

The guiding catheters, and particularly the first guiding catheter, are preferably provided with relatively stiff proximal and shaped distal sections with a more flexible intermediate section which is configured to be disposed within the patient's aortic arch during the procedure as described in copending application Ser. No. 08/813,503 entitled CATHETER WITH FLEXIBLE INTERMEDIATE SECTION and filed on Mar. 7, 1997, which is incorporated herein by reference. In this manner, the position of the distal end of the optical fiber system will be maintained during the procedure even though the heart is beating.

While forming a passageway through the endocardium into the myocardium of the patient's heart for the purpose of revascularization is of significant interest, the passageway formed into the myocardium may be used for other purposes. For example, therapeutic or diagnostic agents may be introduced into the channel for delivery to the patient's endocardium or myocardium. The therapeutic or diagnostic agent may be incorporated into a biocompatible matrix deposited within the channel for delivery or release over an extended period. When delivering a therapeutic or diagnostic agent to the interior of the channel, the channel forming device may be removed and a catheter with an inner lumen extending the length thereof may be advanced through the inner lumen of the delivery catheter until the distal end of the catheter extends into the channel formed in the wall of the patient's heart. A therapeutic or diagnostic agent may then be delivered through the inner lumen of the catheter and out a port in the distal end into the channel such as described in copending application Ser. No. 08/483,512, filed on Jun. 7, 1995, entitled THERAPEUTIC AND DIAGNOSTIC AGENT DELIVERY which is incorporated herein by reference. The drug delivery catheter may be generally a simple elongated flexible tube with an inner lumen extending therein to a port or opening in the distal end of the catheter. The outer dimensions and surface characteristics are suitable to provide longitudinal movement of the drug delivery catheter within the delivery catheter. The distal extremity of the drug delivery catheter is preferably configured to readily fit into the channel formed in the endocardium and myocardium so that delivery of the therapeutic or diagnostic agent well into the channel is ensured. Systemic delivery of drugs and various therapeutic and diagnostic agents to the ablated tissue can also be employed.

There is evidence which tends to support the position that ablation or insult of heart tissue may, by itself, over the long term enhance or even be a significant factor in the revascularization thereof causing angiogenesis. Thus, other means, including mechanical ablation means and a variety of energy sources such as radio frequency ablation means and ultrasonic ablation means which damage or insult myocardial tissue can be the causal factor in revascularization. For example, an RF energy or an ultrasonic energy system which damages myocardial tissue with or without forming a channel may be used. There is also some evidence that ablation of heart tissue within an ischemic region which is causing the patient discomfort by angina or chest pain, can cause the denervation of the ischemic tissue which results in the termination of the angina. Such pain relief may by itself be a substantial clinical advantage because, without the pain, the patient can resume normal or near normal activity. Denervation minimizes or eliminates the need for debilitating pain medication and allows the patient to exercise which can strengthen the heart tissue resulting in further recovery. These and other advantages of the invention will become more apparent from the following detailed description of the invention, when taken in conjunction with the accompanying exemplary drawings.

DETAILED DESCRIPTION OF THE INVENTION

Figure 1:
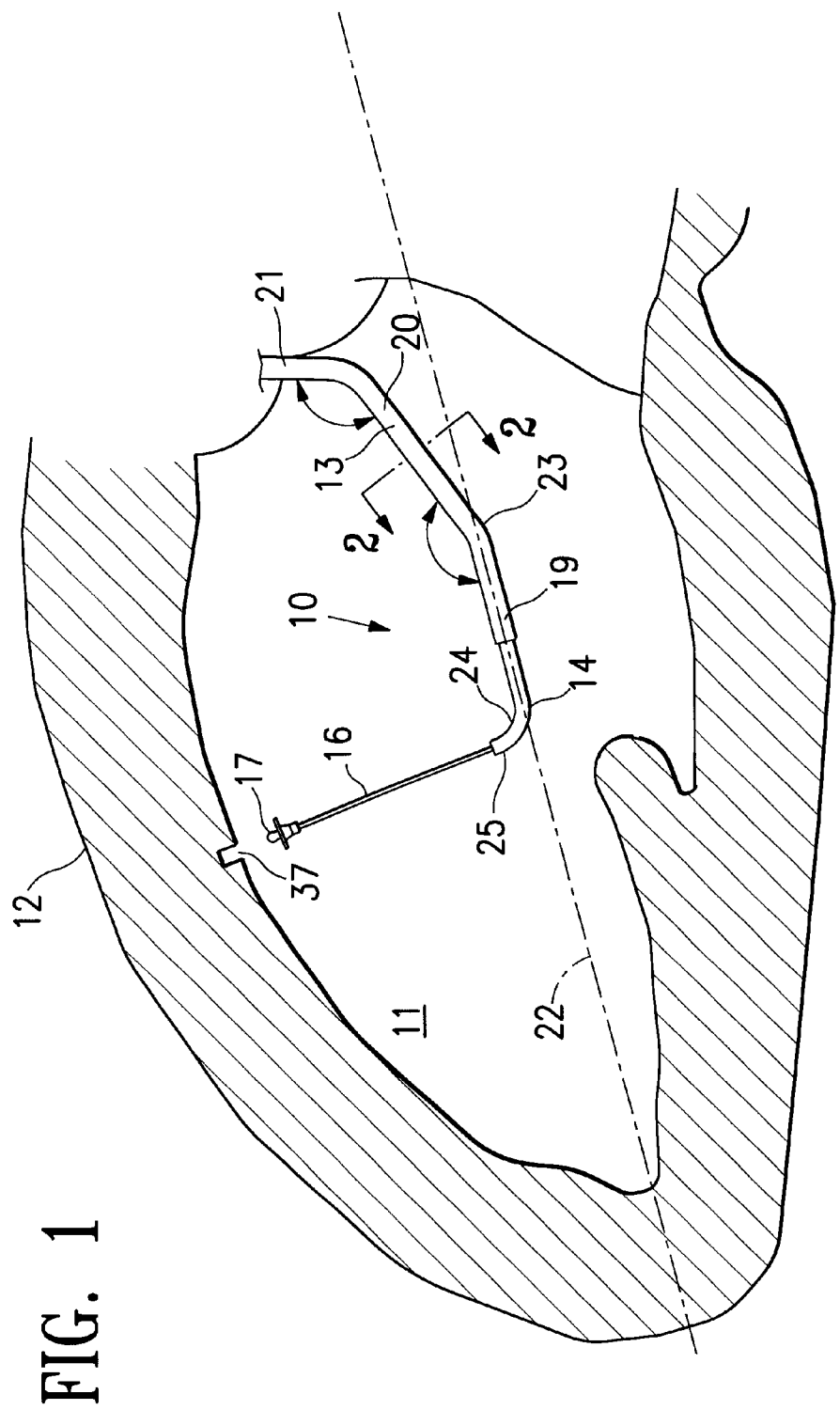
FIG. 1 is an elevational view of a guiding catheter system embodying features of the invention with the distal extremity of the system disposed within the patient's left ventricle, which is seen in a left lateral cutaway view.

FIGS. 1–4 schematically illustrates one presently preferred delivery system 10 of the invention with a distal portion thereof disposed within the left ventricle 11 of a patient's heart 12. The delivery system 10 includes a first guiding catheter 13 and a second catheter 14 slidably and rotatably disposed within the inner lumen 15 (shown in FIG. 2) of the first guiding catheter. An optical fiber 16 with a lens 17 at the distal tip is slidably disposed within the inner lumen 18 (shown in FIG. 2) of the second guiding catheter 14.

Figure 3:
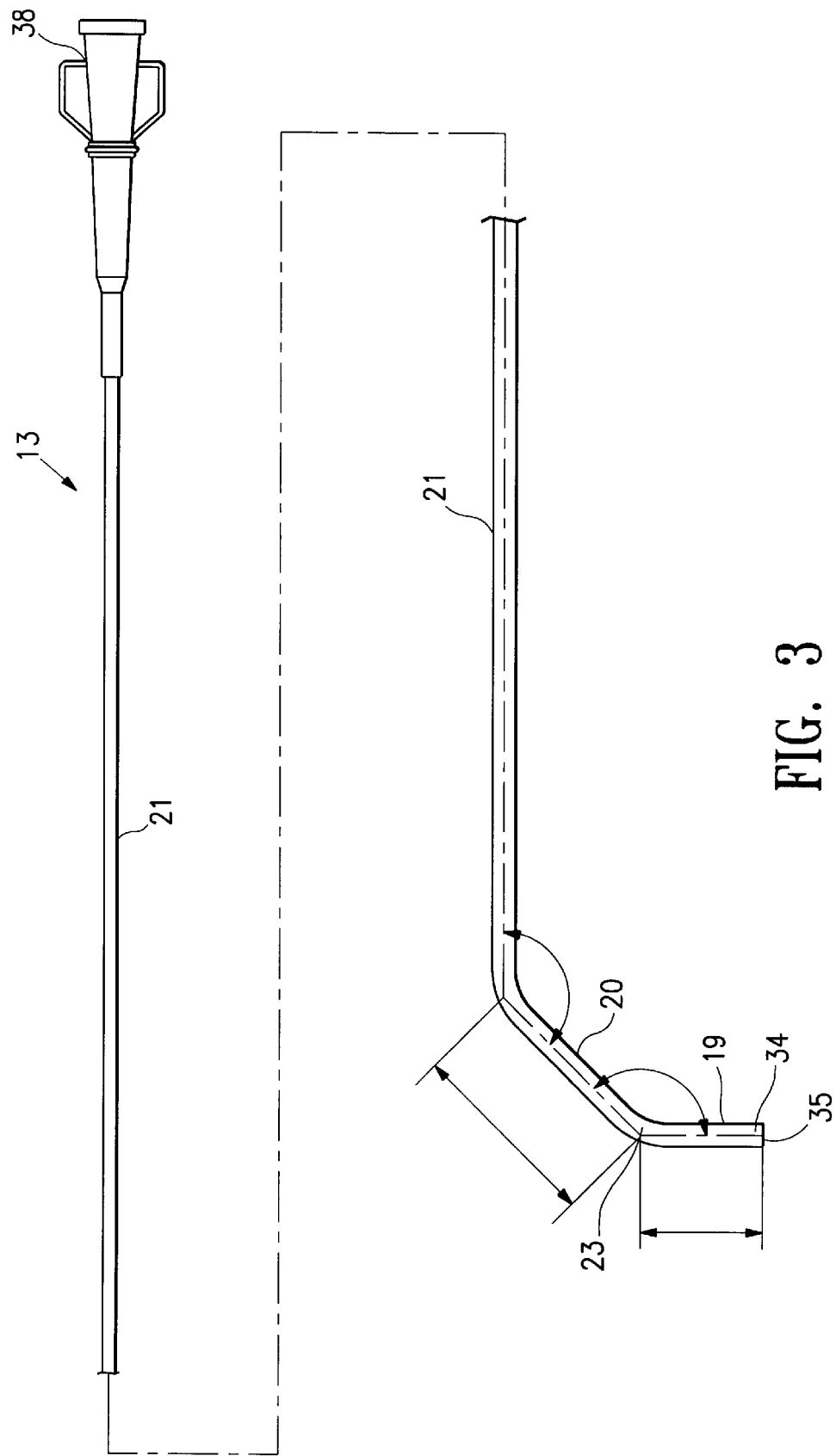
FIG. 3 is an elevational view of the first guiding catheter shown in FIG. 1.

The first guiding catheter 13, as shown in more detail in FIG. 3, has a shaped distal shaft section 23 with two distal segments 19 and 20. The most distal segment 19 is shaped to be at an angle with respect to the proximally adjacent second segment 20 and the second segment 20 is shaped to be at an angle with respect to the proximally adjacent main shaft section 21. The segments of the distal shaft section 23 of the first guiding catheter 13 are angled to discharge the second guiding catheter generally along or parallel with the longitudinal axis 22 of the left ventricle. The second guiding catheter 14, shown in more detail in FIG. 4, has a shaped distal shaft section 24 with a distal segment 25 which is at an angle with respect to the main shaft section 26 of the second guiding catheter to ensure that the discharge axis thereof is perpendicular or near perpendicular with the region of the heart wall in which the procedure is to be performed.

Figure 2:
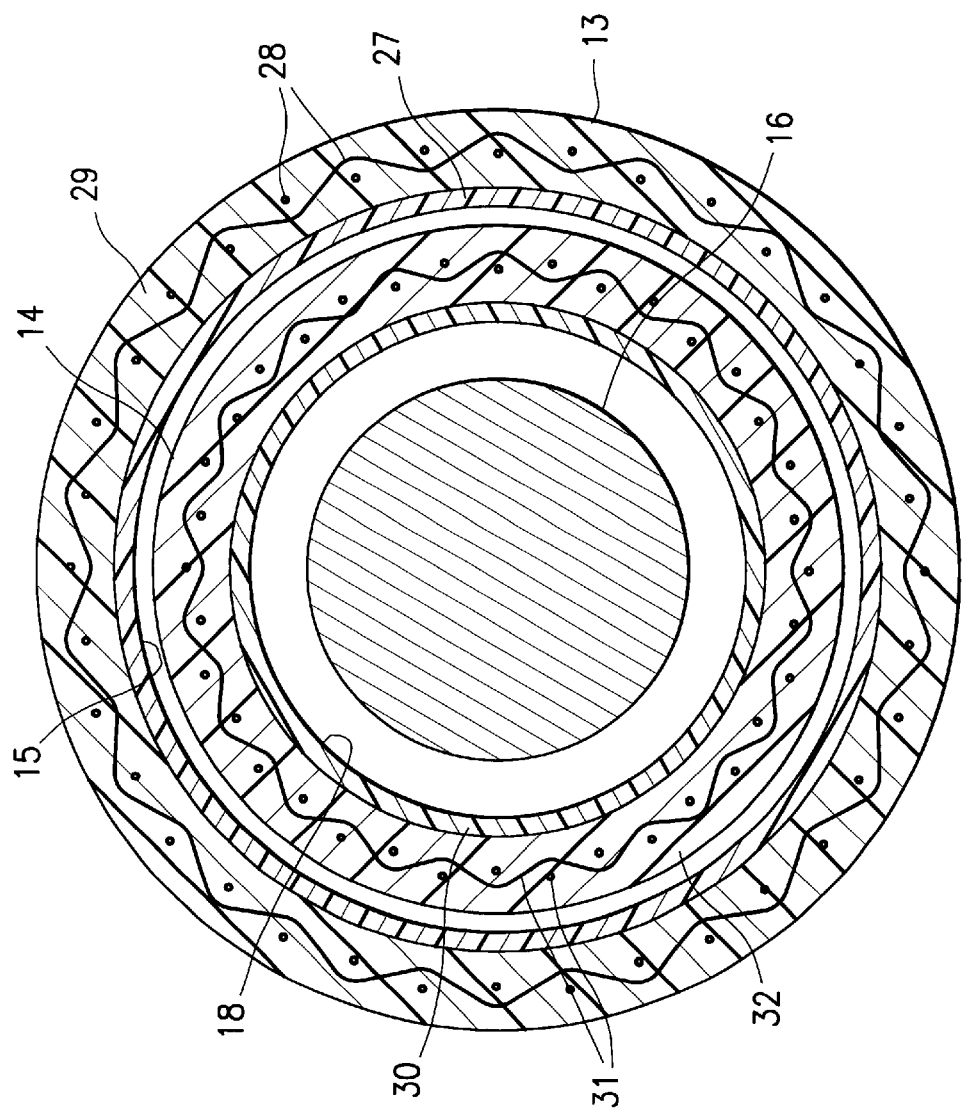
FIG. 2 is a transverse cross-sectional view of the guiding catheter system shown in FIG. 1 taken along the lines 2—2.

As shown in greater detail in FIG. 2, the guiding catheter 13 may be of conventional guiding catheter construction which includes wall structure having a inner lubricous lining 27, a fiber reinforcement 28 in a polymer matrix which may be braided or wound and an outer jacket 29 which may be formed of suitable polymeric material in a conventional manner, e.g. extruding onto the fiber reinforcement. Suitable polymers include polyethylene, polyurethane and the like. The strands of the fiber reinforcement 28 may be stainless steel, or other suitable high strength materials including suitable polymeric materials such as Kevlar® or nylon. The lubricous inner liner 27 may be formed of a suitable fluoropolymer such as poly(tetrafluoro)ethylene which is sold under the trademark Teflon®. An adaptor 38 is provided on the proximal end of the catheter 13 for the introduction of fluids and the second guiding catheter and the like. The overall length of the guiding catheter 13 is about 70 to about 110 cm, the outer diameter is about 0.1 to about 0.15 inch (2.5–3.75 mm) and the diameter of the inner lumen 15 about 0.07 to about 0.1 inch (1.8–2.5 mm).

Figure 4:
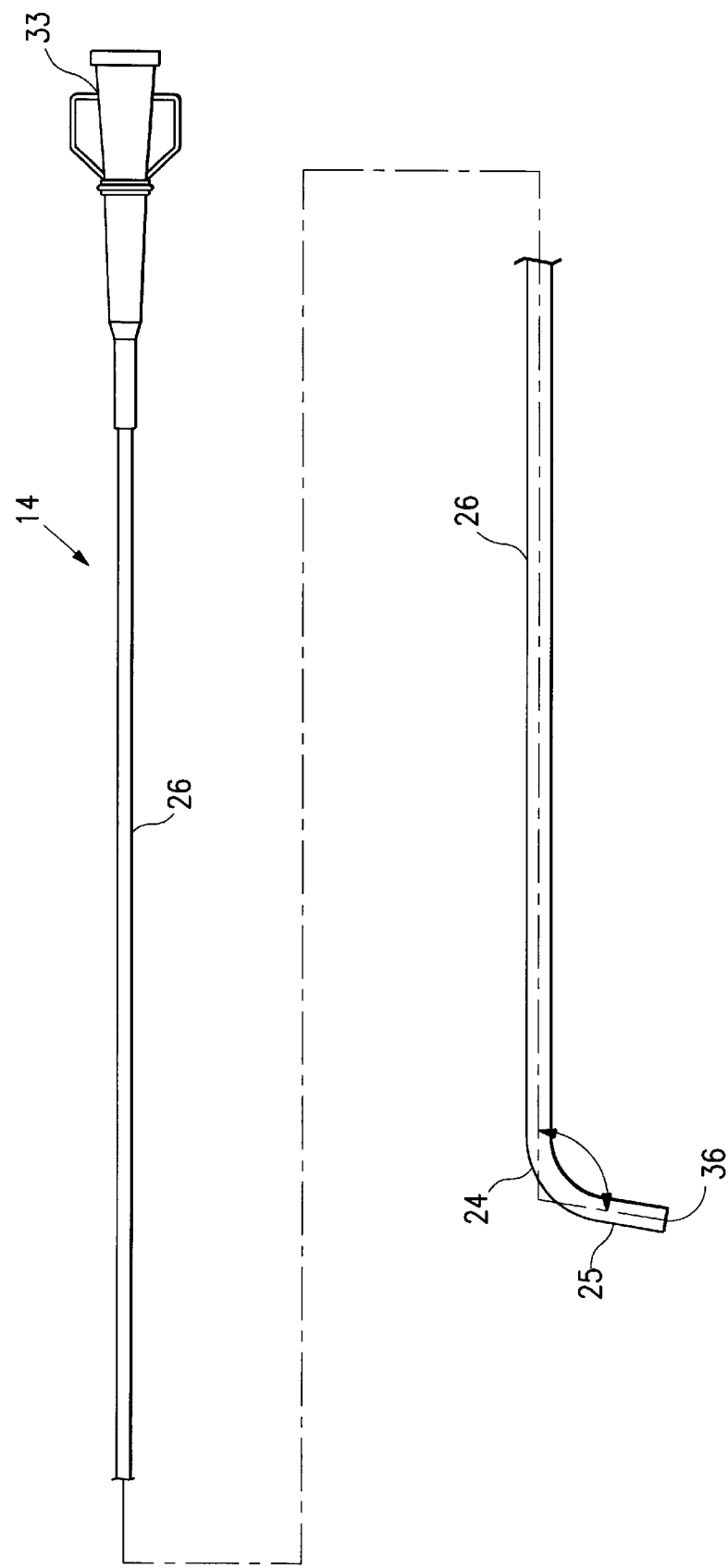
FIG. 4 is an elevational view of the second guiding catheter shown in FIG. 1.

The second guiding catheter 14, as also shown in FIG. 4, has a structure similar to or the same as the guiding catheter 13 and has a lubricious lining 30, a fiber reinforcement 31 which may be braided or wound and an outer polymer jacket 32. The outer diameter of the second guiding catheter 14 is configured so that it can be readily moved longitudinally and readily rotated within the inner lumen 15 of the first guiding catheter 13 by manipulating the proximal end of the second guiding catheter which extends out of the patient. An adapter 33 is provided on the proximal end of the catheter 14 for the introduction of fluids and therapeutic and diagnostic devices. The overall length of the second guiding catheter 14 is about 10 to about 40 cm longer than the guiding catheter 13 to ensure that both the distal end and the proximal end of the second guiding catheter can simultaneously extend out the distal end and the proximal end respectively of the first guiding catheter so that movement of the distal end of the second guiding catheter can be effected by manipulation of the proximal end. The outer diameter of the second guiding catheter 14 is about 0.04 to less than about 0.1 inch (1–2.5 mm) and the diameter of the inner lumen 18 about 0.02 to about 0.07 inch (0.5–1.8 mm). The first guiding catheter 13 may be provided with soft, nontraumatic distal tip 34 to facilitate advancement of the catheter through a patient's vasculature without significant damage to the vessel lining. The second guiding catheter 14 need not have a nontraumatic tip.

The junction between the distal segment 25 and the main shaft section 26 of the second guiding catheter 14 should have a radius of curvature from about 2 to about 30 mm, preferably about 4 to about 20 mm to allow for the passage of a therapeutic or diagnostic device such as optical fiber 16. The radius of curvature need not be constant along the length of the curved section. For example, the curvature can increase progressively in the distal direction along the length of the curved or bent section of the catheter.

In a presently preferred method of the invention, the first guiding catheter 13 is first introduced into the patient's arterial system, preferably by means of the Seldinger technique through the femoral artery and advanced through the patient's arterial system including the aorta until the distal end of the first guiding catheter is disposed at a desired location within the left ventricle 11 generally aligned with or parallel to the longitudinal axis 22 of the left ventricle. The guiding catheter 14 and the optical fiber 16, or other channel forming, therapeutic or diagnostic device, may then be advanced together or sequentially through the inner lumen 15 of the first guiding catheter 13 into the left ventricle. The guiding catheter 14 is advanced out of, rotated within or withdrawn into the inner lumen 15 of the first guiding catheter 13 to orient the distal segment 25 of the second guiding catheter toward a desired region within the left ventricle 11 where the channel is to be formed or the procedure is to be performed. The distal shaft section 24 of the guiding catheter 14 is preshaped so that it forms the desired shape when exiting the port 35 in the distal end of guiding catheter 13. The elongated channel forming or tissue ablation device such as optical fiber 16 may then be advanced through the inner lumen 18 of the second guiding catheter 14 and out the port 36 in the distal end thereof onto the endocardium tissue to form a channel 37 or otherwise ablate tissue therein. Preferably pressure is applied to the channel forming means 16 or other tissue ablation device from its proximal end extending out of the patient so as to maintain contact with the tissue of the heart wall when forming the channel 37 or otherwise ablating tissue. The axial force applied to the proximal end of the optical fiber 16 or other device is preferably sufficient to ensure contact with tissue of the heart wall, but the force should not exceed the level which will cause the operative distal tip of the device to mechanically penetrate heart tissue. Once the channel is formed or tissue is otherwise ablated, the channel forming or ablation device may be withdrawn and repositioned within the left ventricle 11 to form a channel or otherwise ablate tissue at another location within the patient's heart wall.

Generally, the overall length of the optical fiber 16 (or other therapeutic or diagnostic device used) is longer than the second guiding catheter 14 and it is preferably configured to extend out of the second guiding catheter a distance of up to about 15 cm, preferably about 4 to about 10 cm to form the channel 37 or to otherwise perform the desired therapeutic or diagnostic procedure. The optical fiber 16 should have the flexibility required to pass through the inner lumen 18 of the second guiding catheter 14. Further details of optical fibers and laser sources may also be found in U.S. Pat. No. 5,093,877 (Aita et al.), which is incorporated herein in its entirety by reference. The optical fiber 16 may be a single fiber as describe above or a bundle of optical fibers.

Figure 5:
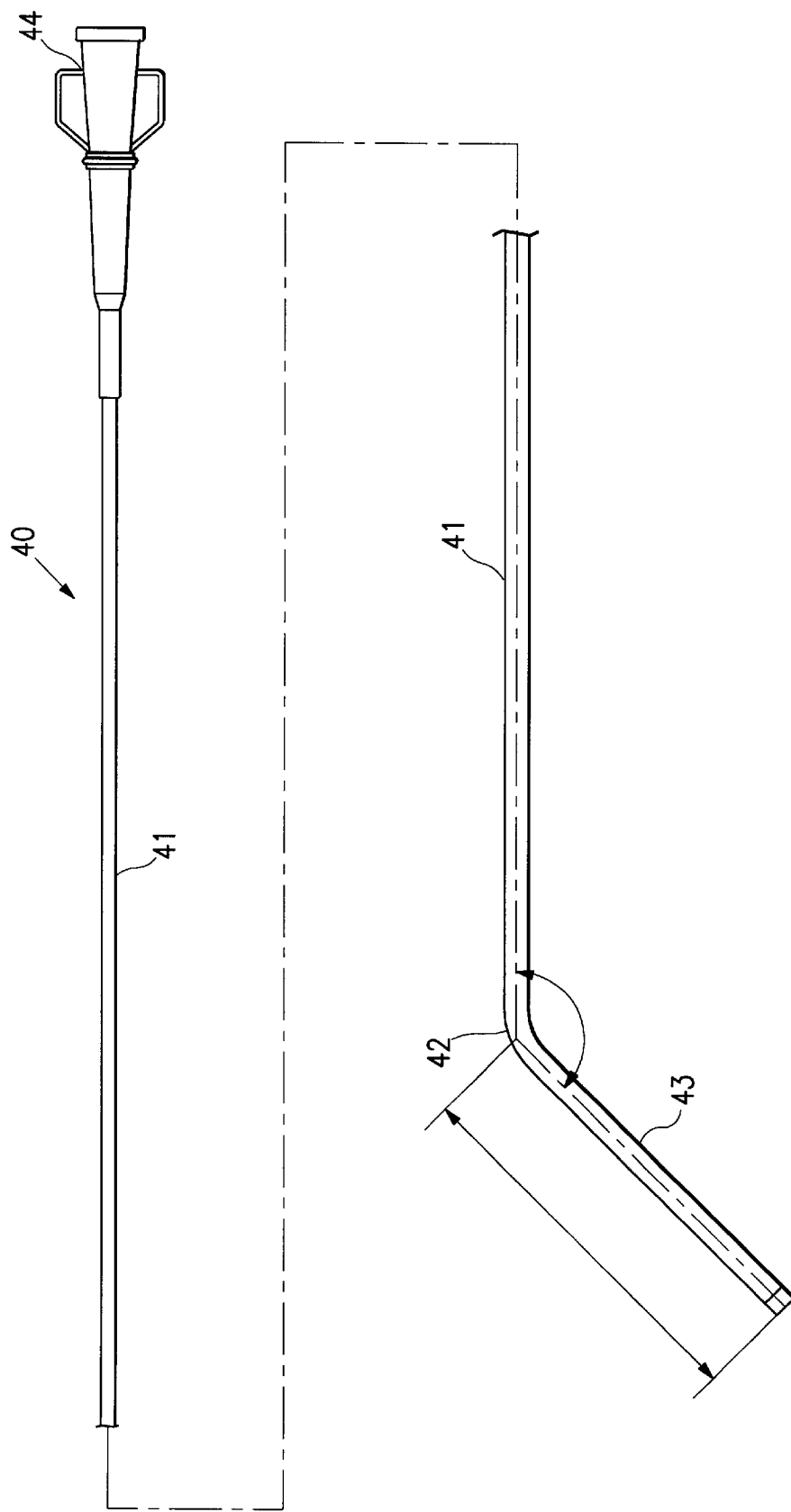
FIG. 5 is an elevational view similar to FIG. 3 of an alternative first guiding catheter having a shaped distal section with a single distal segment.

FIG. 5 illustrates an alternative embodiment of the first guiding catheter 40 which has a main shaft section 41 and a shaped distal shaft section 42 comprising a single angled distal segment 43. An adapter 44 is provided on the proximal end of the main shaft section 41. The structural components and compositions of the first guiding catheter may be the same as found in the first and second guiding catheters 13 and 14 of the first embodiment.

Figure 6:
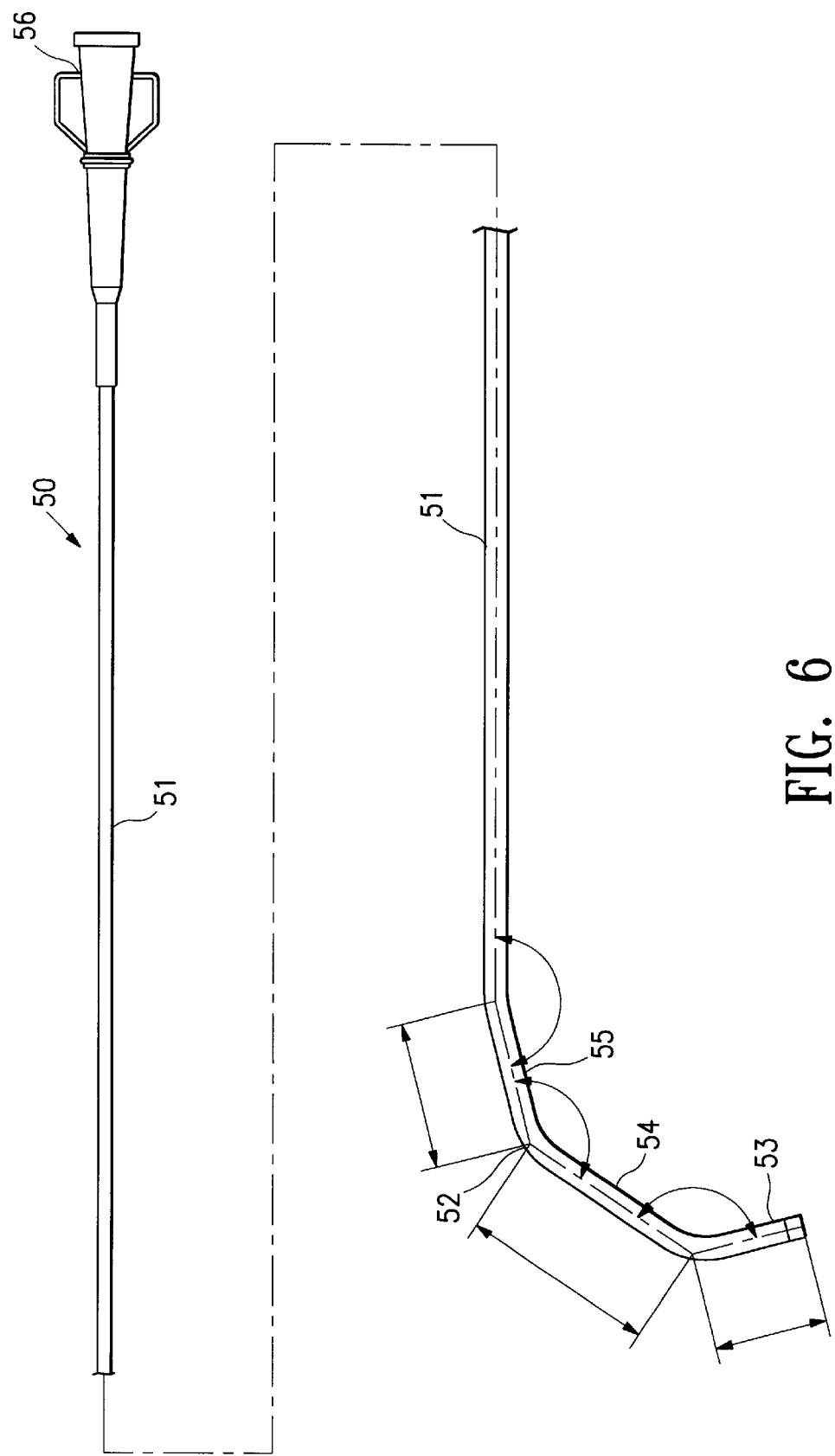
FIG. 6 is an elevational view similar to FIG. 3 of an alternative first guiding catheter having a shaped distal section with three distal segments.

Another alternative embodiment of the invention is shown in FIG. 6 where a first guiding catheter 50 is provided with a main shaft section 51 and a shaped distal shaft section 52 comprising three distal segments, a distal segment 53, an intermediate segment 54 and a proximal segment 55. The distal segment 53 is angled with respect to the intermediate segment 54 and the intermediate segment 54 is angled with respect to the proximal segment 55. An adaptor 56 is provided on the proximal end of the main shaft section 51. The structural components and compositions of the first guiding catheter 50 may be the same as found in the first guiding catheter 13 of the first embodiment.

While the present invention is described herein in terms of certain preferred embodiments, those skilled in the art will recognize that various modifications and improvements may be made to the invention without departing from the scope thereof. For example, a limited number of presently preferred embodiments are given to illustrate various ablation means for forming the channel, whereas the invention may be used to deliver any suitable ablation means even those which may not form a channel but which ablate tissue sufficiently to cause angiogenesis or denervation to minimize angina. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An elongated guiding catheter comprising:
    a) an elongated shaft which has proximal and distal ends, a port in the distal end and an inner lumen extending therein to and in fluid communication with the port in the distal end;
    b) a relatively straight main shaft section; and
    c) a shaped distal shaft section which is distally adjacent the straight main shaft section and which has at least a first segment and a second segment proximally adjacent to the first segment, with the first segment being at an angle of about 95° to about 160° with respect to the proximally adjacent second segment and the second segment being at an angle of about 95° to about 160° with respect to a proximally adjacent third segment or the main shaft section proximally adjacent thereto and which has a discharge axis that will be generally parallel to a longitudinal axis of the patient's left ventricle when the relatively straight main shaft section is disposed in the patient's aorta and the shaped distal shaft section is disposed in the patient's left ventricle.

2. The guiding catheter of claim 1 wherein the first segment is at an angle of about 100° to about 140° with respect to the second segment.

3. The guiding catheter of claim 1 wherein the second segment is at an angle of about 100° to about 140° with respect to an adjacent third segment or the main shaft section adjacent thereto.

4. The guiding catheter of claim 1 wherein the shaped distal shaft section includes a third segment proximally adjacent to the second segment with the third segment being at an angle with respect to the main shaft section proximal thereto of about 110° to about 170° and the second segment being at an angle of about 95 to about 160 degrees with respect to the third segment proximally adjacent thereto.

5. The guiding catheter of claim 1 wherein the distal shaft section includes a third segment proximally adjacent to the second segment with the third segment being at an angle with respect to the main shaft section proximal thereto of about 120° to about 150° and the second segment being at an angle of about 95 to about 160 degrees with respect to the third segment proximally adjacent thereto.

6. The guiding catheter of claim 1 wherein the first segment has a length of about 0.5 to about 5 cm.

7. The guiding catheter of claim 1 wherein the first segment has a length of about 1 to about 4 cm.

8. The guiding catheter of claim 1 wherein the second segment has a length of about 0.5 to about 5 cm.

9. The guiding catheter of claim 1 wherein the second segment has a length of about 1 to about 4 cm.

10. The guiding catheter of claim 1 wherein the length of the shaped distal shaft section is about 2 to about 8 cm.

11. The guiding catheter of claim 1 wherein the length of the shaped distal shaft section is about 4 to about 7 cm.

12. The guiding catheter of claim 1 wherein the shaped distal shaft section has a third segment proximally adjacent to the second segment.

13. The guiding catheter of claim 12 wherein the third segment has a length of about 1 to about 5 cm.

14. The guiding catheter of claim 12 wherein the third segment has a length of about 2 to about 4 cm.

15. A guiding catheter system for the delivery of an elongated device to perform a therapeutic or diagnostic procedure in a region of a patient's heart wall which defines at least in part a left ventricle of the patient's heart, comprising:
   a) a first guiding catheter which has proximal and distal ends, a port in the distal end, an inner lumen extending therein to and in fluid communication with the port in the distal end, a relatively straight main shaft section and a shaped distal shaft section having at least one segment forming an angle with respect to a proximally adjacent portion of the main shaft section so that the shaped distal shaft section has a discharge axis which will be generally parallel to a longitudinal axis of the patient's left ventricle when the main shaft section is disposed in the patient's aorta and the shaped distal shaft section is disposed in the patient's left ventricle; and
   b) a second elongated guiding catheter which is slidably and rotatably disposed within the inner lumen of the first guiding catheter, which is longer than the first guiding catheter and which has proximal and distal ends, a port in the distal end, an inner lumen extending to and in fluid communication with the port in the distal end configured to slidably receive an elongated ablation device, an elongated main shaft section at least a portion of which is aligned with the discharge axis of the first guiding catheter and a distal section configured to have a discharge axis at an angle of about 80° to about 135° with respect to the portion of the main shaft section thereof aligned with the discharge axis of the first guiding catheter.

16. The guiding catheter system of claim 15 wherein the distal section of the second elongated guiding catheter is configured to have a discharge axis at an angle of about 90° to about 120° with respect to the portion of the main shaft section thereof aligned with the discharge axis of the first guiding catheter.

17. The guiding catheter system of claim 15 wherein the shaped distal shaft section of the first guiding catheter has a first segment at an angle of about 95° to about 160° with respect to a proximally adjacent second segment and the second segment is at an angle of about 95° to about 150° with respect to a proximally adjacent third segment or the main shaft section proximally adjacent thereto.

18. The guiding catheter system of claim 15 wherein the shaped distal shaft section of the first guiding catheter has a first segment that is at an angle of about 100° to about 140° with respect to a proximally adjacent second segment.

19. The guiding catheter system of claim 15 wherein the one segment is at an angle of about 95° to about 160° with respect to the proximally adjacent main shaft section.

20. The guiding catheter system of claim 15 wherein the one segment is at an angle of about 100° to about 140° with respect to the proximally adjacent main shaft section.

21. The guiding catheter system of claim 15 wherein the one segment has a length of about 3 to about 8 cm.

22. The guiding catheter system of claim 15 wherein the one segment has a length of about 4 to about 6 cm.

23. The guiding catheter of claim 15 wherein the shaped distal shaft section of the first guiding catheter has a first segment forming an angle with respect to a proximally adjacent second segment.

24. The guiding catheter of claim 23 wherein the shaped distal shaft section of the first guiding catheter includes a third segment proximally adjacent to the second segment with the third segment being at an angle with respect to the main shaft section proximal thereto of about 110° to about 170°.

25. The guiding catheter system of claim 23 wherein the first segment of the shaped distal shaft section of the first guiding catheter has a length of about 0.5 to about 5 cm.

26. The guiding catheter system of claim 23 wherein the first segment of the shaped distal shaft section of the first guiding catheter has a length of about 1 to about 4 cm.

27. The guiding catheter system of claim 23 wherein the second segment of the shaped distal shaft section of the first guiding catheter has a length of about 0.5 to about 5 cm.

28. The guiding catheter system of claim 23 wherein the second segment of the shaped distal shaft section of the first guiding catheter has a length of about 1 to about 4 cm.

29. The guiding catheter of claim 23 wherein the length of the shaped distal shaft section of the first guiding catheter is about 2 to about 8 cm.

30. The guiding catheter of claim 23 wherein the length of the shaped distal shaft section of the first guiding catheter is about 4 to about 7 cm.

31. The guiding catheter system of claim 23 wherein the shaped distal shaft section of the first guiding catheter includes a third segment proximally adjacent to the second segment with the third segment being at an angle with respect to the main shaft section proximal thereto of about 120° to about 150°.

32. The guiding catheter system of claim 31 wherein the third segment of the shaped distal shaft section of the first guiding catheter has a length of about 1 to about 5 cm.

33. The guiding catheter system of claim 31 wherein the third segment of the shaped distal shaft section of the first guiding catheter has a length of about 2 to about 4 cm.

34. A system for percutaneously delivering an elongated ablation device to a left ventricle of a patient's heart, comprising:
   a) a first guiding catheter having an elongated shaft which has proximal and distal ends, a port in the distal end and an inner lumen extending therein to and in fluid communication with the port in the distal end, a relatively straight main shaft section and a shaped distal shaft section with a plurality of segments including at least a first segment, a second segment proximally adjacent to the first segment at an angle of about 95° to about 160° with respect to the first segment and at an angle of about 95° to about 160° with respect to a proximally adjacent third segment or the main shaft section proximally adjacent thereto so that the shaped distal shaft section has a discharge axis which is generally parallel to the longitudinal axis of the patient's left ventricle when the main shaft section is disposed in the patient's aorta and the shaped distal shaft section is disposed in the patient's left ventricle; and b) a second elongated guiding catheter which is slidably and rotatably disposed within the inner lumen of the first guiding catheter, which is longer than the first guiding catheter and which has proximal and distal ends, a port in the distal end, an inner lumen extending to and in fluid communication with the port in the distal end configured to slidably receive an elongated ablation device, an elongated main shaft section at least a portion of which is aligned with the discharge axis of the first guiding catheter and a distal section configured to have a discharge axis at an angle of about 80° to about 135° with respect to the portion of the main shaft section thereof aligned with the discharge axis of the first guiding catheter.

35. The system of claim 34 further comprising a drug delivery catheter disposed within the inner lumen of the second delivery catheter.

36. The system of claim 34 wherein the first segment of the shaped distal shaft section of the first guiding catheter is at an angle of about 100° to about 135° with respect to the second segment.

37. The system of claim 34 wherein the second segment of the shaped distal shaft section of the first guiding catheter is at an angle of about 100° to about 135° with respect to a proximally adjacent third segment or the main shaft section adjacent thereto.

38. The system of claim 34 wherein the shaped distal shaft section of the first guiding catheter includes a third segment proximally adjacent to the second segment, the third segment being at an angle with respect to the main shaft section proximal thereto of about 110° to about 170° and the second segment being at an angle of about 95 to about 160 degrees with respect to the third segment proximally adjacent thereto.

39. The system of claim 34 wherein the shaped distal shaft section of the first guiding catheter includes a third segment proximally adjacent to the second segment, the third segment being at an angle with respect to the main shaft section proximal thereto of about 120° to about 150° and the second segment being at an angle of about 95 to about 160 degrees with respect to the third segment proximally adjacent thereto.

40. The system of claim 34 wherein the first segment of the shaped distal shaft section of the first guiding catheter has a length of about 0.5 to about 5 cm.

41. The system of claim 34 wherein the first segment of the first guiding catheter has a length of about 0.5 to about 5 cm.

42. The system of claim 34 wherein the first segment of the first guiding catheter has a length of about 0.5 to about 4 cm.

43. The system of claim 34 wherein the second segment of the first guiding catheter has a length of about 0.5 to about 5 cm.

44. The system of claim 34 wherein the second segment of the first guiding catheter has a length of about 0.5 to about 4 cm.

45. The system of claim 34 wherein the length of the first and second segments of the first guiding catheter is about 2 to about 6 cm.

46. The system of claim 34 wherein the shaped distal shaft section of the second guiding catheter is configured to have a discharge axis at an angle of about 90° to about 120° with respect to the portion of the main shaft section thereof aligned with the discharge axis of the first guiding catheter.

47. The system of claim 34 including an elongated ablation device disposed within the inner lumen of the second guiding catheter.

48. The system of claim 47 wherein the ablation device comprises an RF ablation system.

49. The system of claim 47 wherein the ablation device comprises an ultrasound ablation system.

50. The system of claim 34 wherein the distal shaft section has a third segment between the main shaft section and the second segment of the distal shaft section.

51. The system of claim 50 wherein the third segment has a length of about 2 to about 4 cm.

52. The system of claim 50 wherein the third segment has a length of about 1 to about 5 cm.

53. The system of claim 52 where in the total length of the first, second and third segments is about 3 to about 8 cm.

54. The system of claim 52 where in the total length of the first, second and third segments is about 4 to about 7 cm.

* * * * *